United States Patent [19]

Kelley

[11] Patent Number: 5,020,711
[45] Date of Patent: Jun. 4, 1991

[54] POUCH FOR REUSABLE HOT/COLD PACKS FOR MEDICAL USAGE

[76] Inventor: Jerry S. Kelley, 126 Tudor Ave., Akron, Ohio 44312

[21] Appl. No.: 431,543

[22] Filed: Nov. 3, 1989

[51] Int. Cl.$^5$ .......................... A45C 13/30; A61F 7/00
[52] U.S. Cl. .................................. 224/222; 224/901; 128/402
[58] Field of Search .............. 224/901, 222, 219, 227, 224/267, 221; 128/399, 402, 403

[56] References Cited

U.S. PATENT DOCUMENTS

| | | | |
|---|---|---|---|
| 2,606,005 | 8/1952 | Poux | 128/402 |
| 3,178,559 | 4/1965 | Fogel et al. | 128/399 |
| 4,079,767 | 3/1978 | Howard | 224/901 |
| 4,347,848 | 9/1982 | Hubbard et al. | 128/402 |
| 4,527,566 | 7/1985 | Abare | 128/403 |

Primary Examiner—Henry J. Recla
Assistant Examiner—David J. Walczak
Attorney, Agent, or Firm—Oldham & Oldham Co.

[57] ABSTRACT

A holder for reusable hot/cold packs used topically for the thermo treatment of muscle injuries, aches, inflammations and the like. Each holder is capable of accepting and retaining a corresponding thermo pack. The holder/thermo pack may be used singularly or combined with one or more like holder/thermo packs using a number of corresponding hook and loop strips for treating larger injury areas. One or more elastic bands, affixed at one end to the holder, wrap around the portion of the body being treated, and attach again to the holder by means of a hook and loop fastener system. If the attached elastic bands are not of sufficient length to completely wrap around the treatment area, additional elastic bands of greater length, with hook and loop fasteners on each end, are used and attached to either the holder or an elastic band.

10 Claims, 2 Drawing Sheets

POUCH FOR REUSABLE HOT/COLD PACKS FOR MEDICAL USAGE

TECHNICAL FIELD

The present invention relates to a holder for a thermo transfer pack used topically for the thermo treatment of patients.

BACKGROUND OF THE INVENTION

Ice packs and hot water bottles have been around for a long time. Their therapeutic usefulness for treatment of aches, pains, sprains, and the like, have taken on new significance in the field of medicine, particularly so-called sports medicine.

The healing process of torn muscle and connective tissue has been scrutinized by the practitioners of sports medicine to allow the recuperation of injured athletes as quickly as possible.

The severe stress imposed on particular body parts, especially joints, by modern sports, particularly professional and highly competitive sports, has subjected certain athletes to an almost constant recuperative regimen to restore vitality to the affected area.

It is unnatural for the body to be subjected to such strenuous repetitive action of a particular type. For example, pitching a baseball, or stroking a tennis ball employs a natural movement, and damage may occur when one does such activity whether in serious competition or on an occasional basis as a form of recreation. In addition to the application of heat and cold to sports injuries, such treatment is often recommended for ailments such as arthritis as well as ordinary bumps, bruises or strains.

Thermo packs from sub-freezing cold to almost scalding are used to speed and enhance the healing process. Some treatment regimens prescribe alternation of hot and cold to stimulate the restorative process.

Pouches, holders, or coverings for use with heating pads, hot water bottles, and hot/cold packs are well known. The pouch or covering is normally used as a barrier between the thermo pack and the user's skin. This barrier serves several purposes. It may be used to hold moisture when used in conjunction with a hot pack for the purpose of administering moist heat. The holder or barrier may extend the pack's useful life by protecting the pack from sharp objects, etc. which may puncture or tear the pack. Another important use of the pouch is to protect the user's skin from injury due to the extremes of hot or cold temperature which the pack may exhibit.

The present invention is a holder which serves all of the above mentioned functions. Additionally, the holder allows the user to apply a pack to any of a number of places on the body and hold the pack in such a position using an elastic band and a hook and loop adhesive means. The present invention is designed in such a way that the holder may be used alone or in combination with one or more additional holders to apply thermo treatments to a larger area.

SUMMARY OF THE INVENTION

The present invention, generally stated, provides a new holder for use with thermo transfer packs, used in topically treating patients with muscle injuries, aches, inflammation and the like.

In one general embodiment, the holder for use with a thermo transfer pack, is made of cloth material, essentially rectangular in shape, open at one end, and slightly larger than the corresponding thermo pack. The thermo pack is slid into the holder and retained there by sealing with closing means. The holder/pack combination is placed on a portion of the user's body for the purpose of applying hot or cold treatment to the area. Elastic bands affixed at one end to the holder wrap around the portion of the body being treated and attach again to the holder by means of a hook and loop fastener system. Hook and loop fasteners are well known in the art and are sold commercially under products names such as Velcro ®. In the event that the bands affixed to the holder are not of sufficient length to completely wrap around the treated area, additional elastic bands of greater length with hook and loop fasteners at each end are used and attached to either the holder or an elastic band.

Hook and loop strips are placed at the top and bottom of each holder for securing the holder by attaching to the corresponding hook and loop strips on the elastic bands. These hook and loop strips may also be used to combine more than one holder in an essentially modular system for applying treatment to a wider area. To achieve this, both holders are placed side by side, so that the elastic bands of one holder rest on the top of the second holder. The hook and loop fasteners of the bands on one holder are secured to the corresponding hook and loop fasteners on the second holder. Elastic bands of the second holder are used to secure the holders to the treated area and, after encircling the body part, are fastened to the first holder by conventional hook and loop means.

Holders can also be combined in such a way as to apply treatment to a longer area. Hook and loop strips placed along the top and bottom edge of a holder are connected to the hook and loop strips on the top or bottom edge of additional holders.

It is an object of this invention to provide a holder for a thermo pack, such that said holder may be used alone or in combination with one or more additional holders to apply thermo treatment to an area of the body regardless of size.

It is also an object of this invention to provide a holder for a thermo pack, such that said holder creates a barrier between the thermo pack and the user's skin.

It is an object of this invention to provide a holder for a thermo pack, such that said holder may be used to hold moisture when used in conjunction with a hot pack for the purpose of administering moist heat.

It is a further object of this invention to provide a holder for a thermo pack which protects the pack from damage, thereby extending the holder's useful life.

It is also an object of this invention to provide a holder for a thermo pack such that the thermo pack could be secured to a plurality of treatment areas on the user's body.

It is a further object of this invention to provide a holder for a thermo pack such that the holder be of low cost and long life upon repeated usage and temperature fluctuations.

These and other objects and advantages of the present invention will become more readily apparent from the more detailed description of the preferred embodiments taken in conjunction with the drawings and are achieved by: a holder for a thermo transfer pack used for variant temperature treatment comprising: a flexible envelope, the boundary of which is defined by a perimeter and having an open means extending along a portion of the perimeter thereof; said pouch being dimensioned slightly larger than the thermo transfer pack such that the thermo transfer pack can be inserted into said holder; a closing means located along the open means of said holder for the purpose of retaining said thermo pack in said holder until removed; a plurality of securing sites, said sites located in a plurality of positions on the exterior of the holder; a plurality of bands affixed to the exterior of said holder, said bands having first and second ends wherein said first end is affixed to the holder and the second end has a plurality of securing means on at least one side such that it is capable of being attached to a securing site on the holder; said holder when used with a single thermo pack is capable of being held onto a treatment area by wrapping said bands around the body and affixing the securing means of said bands to any corresponding securing site on the holder.

DETAILED DESCRIPTION OF THE PREFERRED EMBODIMENT

Figure 1:
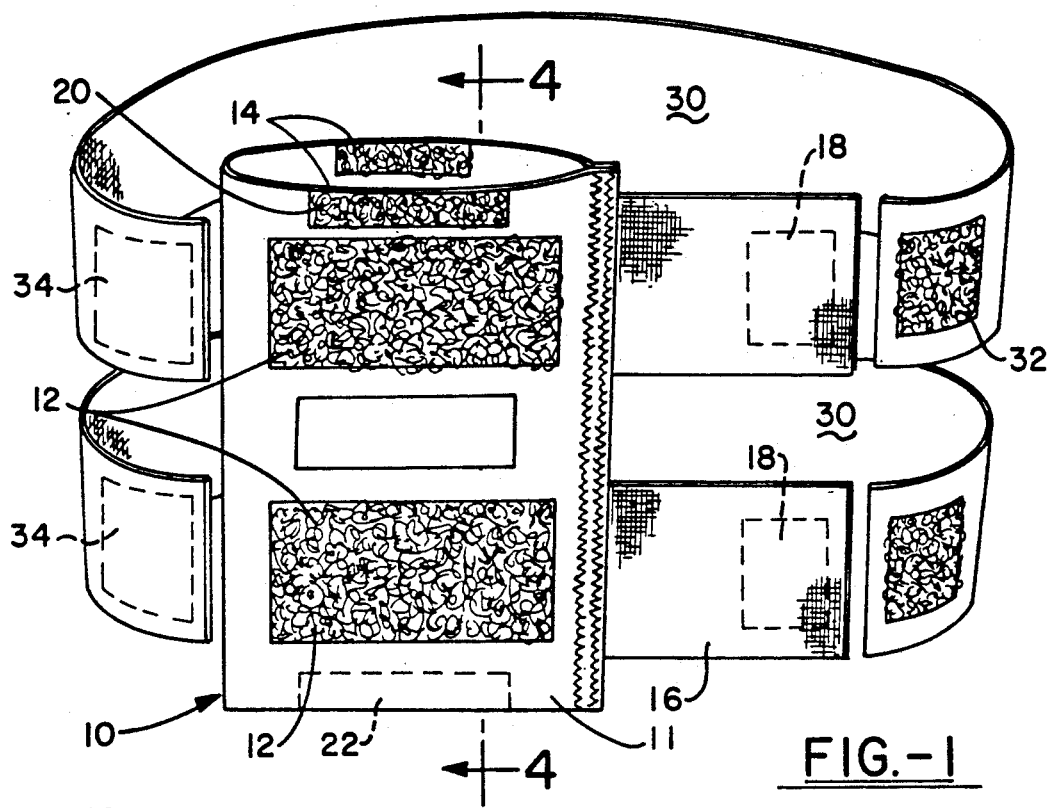
FIG. 1 is a perspective view of one embodiment of a holder for a thermo transfer pack and an attachable extension band.

Now with reference to the invention illustrated in the drawings, and looking particularly at FIG. 1, the figure shows a perspective view of the holder for a thermo transfer pack.

The holder 10 for a thermo transfer pack 50 comprises an envelope 11, a closing means 14 at the open end of the holder 10, two securing pads 12 on the front surface of the holder 10, a securing strip 20 on the top edge of the front surface of the holder 10, a securing strip 22 on the bottom edge of the back surface of the holder 10, two elastic bands 16, each band attached to the holder 10 at one end, and a securing pad 18 on the back surface of each band.

The envelope 11 is an essentially rectangular shaped container made of a breathable cloth material and open at one end. The cloth material is contemplated as cotton, polyester, or a blend of the two, although any other material known in the art could be used. The envelope 11 is of a size that is slightly larger than the thermo pack which is to be contained within said holder. The thermo pack is slid into the envelope 11 and held inside the holder 10 by a closing means 14 consisting of parts 14a and 14b on the inside of holder 10.

The closing means 14 is shown as a two part hook and loop fastener system, shown as 14a and 14b, which is well known in the art. Hook and loop fasteners are known and sold commercially under such product names as Velcro ®. However, a series of snaps, a zipper, or the like could be used in place of the hook and loop. An alternative embodiment contemplates a holder 10 which does not permit removal of the thermo pack by the user. In this embodiment, the open end of the holder is sealed once the thermo pack is inserted, thus eliminating the need for a closing means 14 as discussed above. The unit would be regenerated by heating or chilling the entire unit instead of the thermo pack itself.

Two securing sites 12, shown as hook and loop pads are placed on the front surface of the holder 10. The pads 2 are shown as essentially rectangular in shape and are of a size sufficient to receive any corresponding hook and loop pad. However, a number of various shapes and sizes of such pads could be contemplated.

Two elastic bands 16 are also shown in FIG. 1 with each band being attached to the holder 10 at one end. Two securing means shown as hook and loop pads 18 are placed on the back surfaces of elastic bands 16. These pads are shown as a single piece of hook and loop, essentially rectangular in shape although the number and shape of such pads can vary. The pads 18 on bands 16 are designed such that they can engage hook and loop pads 12 on holder 10 or any other corresponding pad necessary for the use of the holder for the thermo pack.

A securing strip 20 is placed on the top edge of the front surface of the holder 10. A securing strip 22 is placed on the bottom edge of the back surface of the holder 10. Both securing strips 20 and 22 are made of hook and loop and shown as essentially rectangular in shape. However, the number and shape of such pads could vary greatly.

Generally, the holder 10 is used to contain a thermo pack 50 which has been previously heated or chilled. Alternatively, in the embodiment which does not contemplate a removable thermo pack the entire unit (the thermo pack and holder) would be tested or chilled prior to use. The holder aids the user by holding the hot/cold thermo pack 50 on the area to be treated.

Another variation of the general embodiment contemplates an insulating means between the thermo pack and the side of the holder 10 which does not contact the body. This insulating means 52 could be permanently affixed to the holder 10. One insulating means 52 contemplated is a type of semi-rigid foam plastic made from polystyrene, polyurethane or any other material known in the art.

This insulating means 52, where utilized, serves to reduce the amount of heat or cold lost through the exposed side of the holder 10. Such energy conservation results in a longer lasting thermo pack 50 or allows the manufacturer to reduce the volume of the thermo pack 50 while achieving the similar effectiveness.

Specifically, the holder 10 receives a hot/cold thermo pack 50 which is slid into the holder. Closing means 14 is sealed in order to hold the thermo pack 50 in place. The holder/thermo pack combination is placed on the area to be treated. The elastic bands 16 are wrapped around a portion of the user's body until the hook and loop pads 18 on the elastic bands 16 engage the hook and loop pads 12 on holder 10, thereby securing the holder/pack combination to the treatment area.

When the holder pack combination is used on a treatment area which is too large for the elastic bands 16 to circumscribe that portion of the user's body, the present invention provides for elastic extension bands 30 which can be added to the holder 10. These elastic bands 30 shown in FIG. 1 are essentially similar in width to elastic bands 16. Extension bands 30 may come in a variety of lengths such that they are sufficient to wrap around or circumscribe the portion of the user's body to which the holder/pack combination will be secured. Extension bands 30 have hook and loop pads 32 on one or more surfaces of each end such that these pads 32 will engage with corresponding pads on either the holder 10 or elastic bands 16.

If the treatment area is too large to be treated using a single thermo pack 50, the holder 10 of the present invention may be combined with additional holders in an essentially modular system to form a larger unit for applying heat or cold. The additional holders have dimensions and characteristics identical to the original holder 10.

Figure 2:
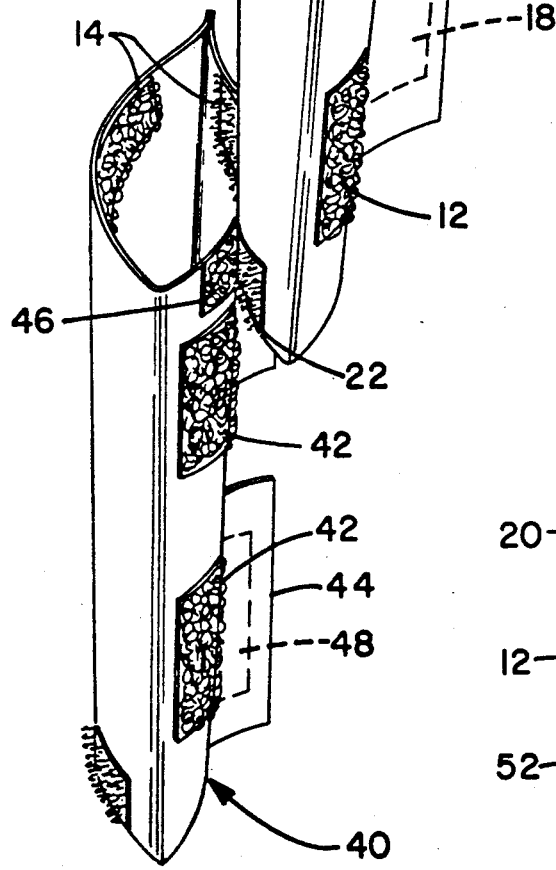
FIG. 2 is a perspective view of the use of a holder for a thermo transfer pack whereby two or more holders may be attached in an end-to-end manner.
Figure 4:
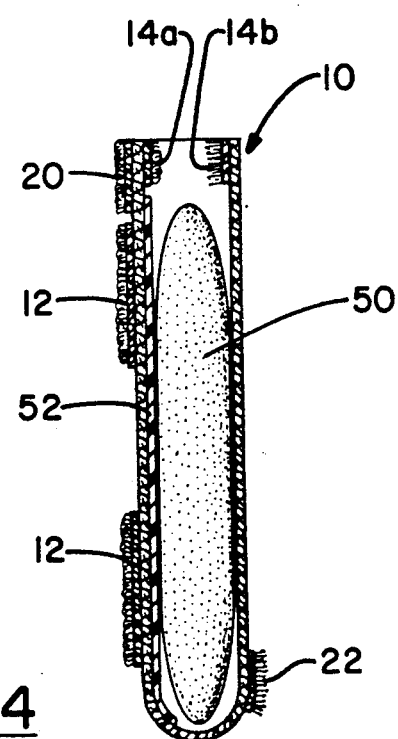
FIG. 4 is a longitudinal cross section of one embodiment of a holder for a thermo transfer pack with the pack and insulating means contained therein. This cross section is cut along line 4—4 in FIG. 1.

When it is necessary to treat a long, narrow area of the body, two or more holders can be attached end to end. This is accomplished by placing the bottom edge of one holder 10 over the top edge of a second holder 40 as shown in FIG. 2, such that the bottom hook and loop strip 22 of holder 10 engages with the top hook and loop strip 46 of holder 40. This unit may be held to the treatment area using the elastic bands 16 on the pouch, using extension bands 30 or any combination thereof.

Figure 3:
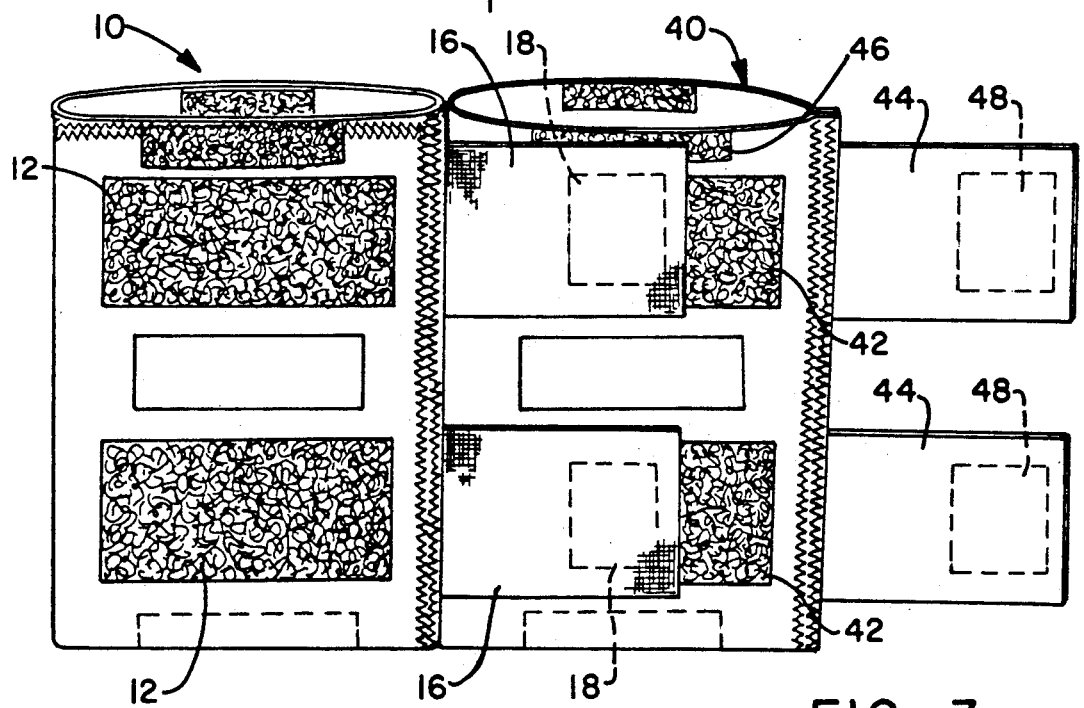
FIG. 3 is a perspective view of the use of a holder for a thermo transfer pack whereby two or more holders may be attached in a side to side manner.

When it is necessary to treat an area wider than one holder, two or more holders can be attached in a side by side manner as shown in FIG. 3. This is accomplished by placing at least two holders next to each other with the open end of each holder facing the same direction. The elastic bands 16 of holder 10 should engage the hook and loop pads 42, of an additional holder, 40. The elastic bands 44 of the additional holder 40, which is not connected to an adjacent holder, can be used to wrap around or circumscribe the portion of the user's body to which the holder/pack combination is to be secured.

Additionally if an extremely large area of the body is to be treated the method of attaching two or more holders illustrated in FIG. 2 can be combined with the method in FIG. 3, yielding a large number of possible combinations.

The hook and loop pads 18 on bands 16 are then engaged with the corresponding hook and loop pads 12 of holder 10 to hold the holder/pack combination onto the treatment area. In the event that bands 16 are not of sufficient length, extension bands 30 may be used.

While in accordance with the patent statutes the best mode and preferred embodiment of the invention has been described, it is to be understood that the invention is not limited thereto, but rather is to be measured by the scope and spirit of the appended claims.

What is claimed is:

1. A holder for a thermo transfer pack use for variant temperature treatment and capable of being attached to an adjacent similar holder comprising:
   at least one flexible envelope, the boundary of each said envelope being front side a back side and a defined by a perimeter having a top, a bottom and side edges and having an open area extending along a portion of the perimeter thereof; each said envelope being dimensioned slightly larger than a corresponding thermo transfer pack such that a transfer pack can be inserted into each envelope;
   a closing means located along at least a portion of the open area of each holder for retaining each thermo pack in said holder until removed;
   a plurality of securing sites, said sites located along the top edge, the bottom edge and on the front side of each envelope;
   a plurality of bands, said bands having first and second ends wherein said first end is affixed to the envelope and the second end has securing means on at least one side, thereof; whereby one of said holders can be attached to an adjacent holder either in a vertical configuration by attaching said securing site along the top edge of one envelope to the securing site along the bottom edge of a second envelope or in a horizontal configuration by attaching the securing means at the ends of said bands to the securing site of the front side of an adjacent holder.

2. The holder for a thermo transfer pack as recited in claim 1 wherein the closing means for retaining said thermo pack is reusable and retains said thermo pack in said holder until removed.

3. The holder for a thermo transfer pack as recited in claim 2 wherein the closing means for retaining said thermo pack comprises corresponding pieces of hook and loop fasteners.

4. The holder for a thermo transfer pack as recited in claim 1 wherein the securing sites and recuring means comprise corresponding pieces of hook and loop fasteners.

5. The holder for a thermo transfer pack of claim 1 wherein the bands are made of elastic..

6. The holder for a thermo transfer pack as recited in claim 1, further comprising a plurality of extension bands adapted for use with the bands of said holder for wrapping around larger body portions; said extension bands have a first and second ends with securing means on one side of each end with said securing means facing in opposite directions such that said extension bands are attached to securing sires on front side at the holder and ends of the bands.

7. The holder for a thermo pack as recited in claim 6 wherein the extension bands are made of elastic.

8. The holders for thermo transfer packs as recited in claim 1 wherein the extension bands are made of elastic.

9. A holder for thermo transfer packs as recited in claim 1 wherein said holder further comprises an insulating means to reduce the amount of heat or cold lost during treatment.

10. A modular system of holders for thermo transfer packs used for variant temperature treatment comprising:
    a plurality of holders, each having at least one flexible envelope, the boundary of each said envelope being defined by a front side, a back side and a perimeter having a top, a bottom and side edges and having an open area extending along a portion of the perimeter thereof; each said envelope being dimensioned slightly larger than a corresponding thermo transfer pack such that a transfer pack can be inserted into each envelope;
    a closing means located along at least a portion of the open area of each holder for retaining each thermo pack in said holder until removed;
    a plurality of securing sites, said sites located along the top edge, the bottom edge and on the front side of each envelope;
    a plurality of bands, said band having first and second ends wherein said first end is affixed to the envelope and the second end has securing means on at least one side thereof; whereby one of said holders can be attached to an adjacent holder either in a vertical configuration by attaching said securing site along the top edge of one envelope to the securing site along the bottom edge of a second envelope or in a horizontal configuration by attaching the securing means at the ends of said bands to the securing site of the front side of an adjacent holder, wherein said plurality of holders are joined together.

* * * * *

UNITED STATES PATENT AND TRADEMARK OFFICE
CERTIFICATE OF CORRECTION

PATENT NO. : 5,020,711
DATED : June 4, 1991
INVENTOR(S) : Kelley, Jerry S.

It is certified that error appears in the above-indentified patent and that said Letters Patent is hereby corrected as shown below:

Claim 1, Line 1 (column 5, line 46) delete "use" and insert --used--;

Claim 1, line 5 (column 5, line 50) delete "front side a back side and a";

Claim 1, line 6 (column 5, line 51) after "a" insert --front side, a back side and a--.

Claim 4, line 2 (column 6, line 15) delete "recuring" and insert --securing--.

Claim 6, line 8 (column 6, line 27) delete "sires" and insert --sites--; and delete "at" and insert --of--.

Signed and Sealed this

Twenty-eighth Day of December, 1993

Attest:

BRUCE LEHMAN

Attesting Officer     Commissioner of Patents and Trademarks